US008709016B2

(12) United States Patent
Park et al.

(10) Patent No.: US 8,709,016 B2
(45) Date of Patent: Apr. 29, 2014

(54) SURGICAL GUIDE SYSTEM USING AN ACTIVE ROBOT ARM

(75) Inventors: Youngbae Park, Fremont, CA (US); Boris Martin Preising, Palo Alto, CA (US)

(73) Assignee: Curexo Technology Corporation, Fremont, CA (US)

( * ) Notice: Subject to any disclaimer, the term of this patent is extended or adjusted under 35 U.S.C. 154(b) by 314 days.

(21) Appl. No.: 12/966,276

(22) Filed: Dec. 13, 2010

(65) Prior Publication Data

US 2011/0152871 A1    Jun. 23, 2011

Related U.S. Application Data

(60) Provisional application No. 61/284,033, filed on Dec. 11, 2009.

(51) Int. Cl.
*A61B 17/58* (2006.01)

(52) U.S. Cl.
USPC .......................................................... 606/91

(58) Field of Classification Search
USPC .......................................................... 606/91
See application file for complete search history.

(56) References Cited

U.S. PATENT DOCUMENTS

| 7,419,492 B2 | 9/2008 | Yoon et al. |
| 7,591,821 B2 * | 9/2009 | Kelman ........................ 606/84 |
| 2006/0184177 A1 * | 8/2006 | Echeverri ....................... 606/91 |

OTHER PUBLICATIONS

Lewinnek, G.E., et al., Dislocations after Total Hip-Replacement Arthroplasties, The Journal of Bone and Joint Surgery, 1978, 217-220.
Von Knoch, M., et al., Late Dislocation After Total Hip Arthroplasty, The Journal of Bone and Joint Surgery, Nov. 2002, 1949-1953.
Barrack, R.L., Dislocation After Total Hip Arthroplasty: Implant Design and Orientation, Journal of the American Academy of Orthopaedic Surgeons, 2003, 89-99.
Tannast, M., et al., Computer-assisted Simulation of Femoro-acetabular Impingement Surgery, Navigation and MIS in Orthopedic Surgery, 2007, pp. 448-455.
Yoon, Y.S., et al., Resolving inconsistencies in defining the target orientation for the acetabular cup angles in total hip arthroplasty, Clinical Biomechanics, 2008, 253-259.

* cited by examiner

*Primary Examiner* — Nicholas Woodall
(74) *Attorney, Agent, or Firm* — Pandiscio & Pandiscio

(57) ABSTRACT

In this invention, there is provided a system which can visually indicate to the surgeon an ideal angle for the acetabular cup during a total hip replacement procedure, wherein the system uses a robotic system which orients an elongated guide at the preferred axis for the acetabular cup.

8 Claims, 14 Drawing Sheets

Robot tool cutter used for surgeon alignment of acetabular reaming tool.

Orthopilot System Of Aesculap

Screenshots From The Brainlab System

Computer-Guided Surgical Systems For Hip Surgery

Robot tool cutter used for surgeon alignment of acetabular reaming tool.

SURGICAL GUIDE SYSTEM USING AN ACTIVE ROBOT ARM

REFERENCE TO PENDING PRIOR PATENT APPLICATION

This patent application claims benefit of pending prior U.S. Provisional Patent Application Ser. No. 61/284,033, filed Dec. 11, 2009 by Youngbae Park for SURGICAL GUIDE SYSTEM USING AN ACTIVE ROBOT ARM, which patent application is hereby incorporated herein by reference.

FIELD OF THE INVENTION

This invention relates to surgical methods and apparatus in general, and more particularly to surgical methods and apparatus for guiding a surgeon during a surgical procedure.

BACKGROUND OF THE INVENTION

In some surgical procedures, it is necessary to know the proper axis and direction of the surgery in order to achieve the desired surgical result.

By way of example but not limitation, it is necessary to know the proper axis and direction of the surgery when inserting an acetabular cup during a total hip arthroplasty procedure, or when inserting a pedicle screw during spinal surgery, or when cutting the tibia during a total knee arthroplasty procedure, etc.

Acetabular Cup Placement During a Total Hip Arthoplasty Procedure

In a total hip arthroplasty procedure, a damaged hip joint is replaced with an artificial joint. See, for example, FIG. 1, where a prosthetic hip joint 5 is shown installed in a patient.

A total hip arthroplasty procedure may be necessary for a variety of reasons, e.g., severe arthritis, tissue necrosis, trauma, etc. Current prosthetic hip joints are generally able to restore substantially normal function to the hip and eliminate pain for the patient, and can typically function for many years. More than one million total hip arthroplasty procedures are currently performed each year, and various designs and sizes of artificial joints are currently on the market.

Still looking now at FIG. 1, the prosthetic hip joint 5 is primarily composed of an acetabular cup 10 (which is a hemispheric cup installed in the pelvis 15 of the patient) and a ball-and-stem 20 (which is installed in the femur 25 of the patient). It will be appreciated that the structure of the prosthetic hip joint 5 significantly resembles the original anatomy of the hip joint.

To install the acetabular cup 10, the surgeon generally enlarges and shapes the natural cup of the acetabulum (of the pelvis 15) with a surgical tool so as to create a seat for the prosthetic cup 10, and then the prosthetic cup 10 is press-fit into the acetabulum and fixed in place with additional screws or cement. See, for example, the screw 30 which is visible in FIG. 1.

Inasmuch as the acetabular cup 10 is shaped as a hemispherical cup, it is important that the acetabular cup be installed in the acetabulum at the proper angle. Otherwise, the neck 35 of the femoral stem 20 can impinge on the rim 40 of the acetabular cup 10 as the leg is moved relative to the pelvis, e.g., during patient activities such as walking, stair climbing, standing, exercise, etc. Such impingement reduces the range of motion for the joint and can cause pain to the patient. Most surgeons agree that it is extremely important that the acetabular cup be accurately positioned in the acetubulum during a total hip arthroplasty procedure in order to achieve a superior surgical outcome.

Current Computer-Guided Surgical Systems for Aiding Proper Placement of the Acetabular Cup Various computer-guided surgical systems are currently available to aid in the proper placement of the acetabular cup during a total hip arthroplasty procedure.

By way of example but not limitation, the Orthopilot system from Aesculap (USA), and the BrainLab system from Brainlab (Germany), are currently available to aid a surgeon in the proper placement of an acetabular cup during a total hip arthroplasty procedure. See FIGS. 2-4.

In general, existing computer-guided surgical systems consist of an infra-red (IR) camera, a surgical tool with infra-red (IR) marker, and a computer. The IR marker allows the spatial position of the surgical tool to be measured in real-time by the IR camera and computer. The computer also performs the calculations required to compare the real-world position of the surgical tool (determined through the use of the IR camera and IR marker) with a pre-determined computer model of the anatomy and a pre-determined surgical plan, and displays the results on a computer monitor which is located in the operating room so as to guide the surgeon in placing the acetabular cup in the acetabulum. There are also similar computer-guided surgical systems which use magnetic field tracking, or articulated digitizer arms, in place of the aforementioned IR camera and IR markers.

In order for a computer-guided surgical system to provide accurate guidance to the surgeon, the pre-determined computer model of the patient's anatomy must be placed into proper registration with the patient's real-world anatomy. This is typically done by fixing a tracker (which consists of a marker and fixator to track the real-world position of an object) to the pelvis of the patient. This allows the computer to determine the position of the patient's real-world anatomy. Then an anatomical landmark on the pelvis of the patient is digitized. This allows the computer to place the pre-determined computer model of the patient's anatomy into proper registration with the patient's real-world anatomy, since the digitized anatomical landmark is present in both the real-world anatomy and in the pre-determined computer model of the patient's anatomy. And a marker is preferably placed on the surgical tool which is to be used in the surgical procedure. As a result, when required, the computer-guided surgical system can display the current angle of the pelvis and/or surgical tool to the surgeon, and can also display a preferred angle for the prosthetic acetabular cup using a pre-determined surgical plan.

Current computer-guided surgical systems generally require attachment of markers to the surgical tool, which may be cumbersome. Also, additional surgical time is required for installation of the tracker and digitization of the anatomical landmarks. Furthermore, at least in the case of an IR system, a clear line of sight from the IR camera to the IR marker is required, which can limit movement of the surgeon about the patient and/or the positioning of equipment in the operating room. While at least some of these limitations may continue to exist with the novel guidance technology of the present invention, the inventors believe that the benefits which are derived from the present invention more than overcome any remaining limitations.

Another limitation of current computer-guided surgical systems is that a computer monitor is used during the surgical procedure to show the surgeon the preferred angle for the prosthetic acetabular cup. This can present multiple issues for the surgeon when the surgeon is trying to understand and utilize the information provided on the computer monitor by these conventional computer-guided surgical systems.

For one thing, the computer monitor provides only a 2D image to the surgeon, while the actual surgery is performed in the real-world, which is a 3D environment. For another thing, with these prior art computer-guided surgical systems, the surgeon needs to view the surgical site and the computer monitor separately, i.e., one at a time and not simultaneously, since the computer monitor is typically located about 1-2 meters away from the surgical site. Furthermore, in some cases, the view shown on the computer monitor might not be perfectly correlated with the surgical scene, i.e., the right side of the surgical scene may be presented at the left side of the computer monitor, and/or the top side of the surgical scene may be presented at the bottom side of the computer monitor, etc. And it can be difficult to present 2D information on the computer monitor in a manner which gives the surgeon, who is working in the 3D space of the real world, a clear idea of the proper angle for the prosthetic acetabular cup.

Thus it will be seen that it can be a time-consuming and inaccurate process for the surgeon to properly position the acetabular cup in the pelvis using prior art computer-guided surgical systems. In fact, it is commonly reported that prior art computer-guided surgical systems are generally capable of reducing cup placement errors, but they are not capable of completely eliminating cup placement errors.

For example, the surgeon holds the impactor, which is a long surgical tool used to insert the acetabular cup into position in the acetabulum, and looks up at the computer monitor of the prior art computer-guided surgical system. The computer monitor shows the current angle of the impactor (determined using markers on the impactor), and the preferred angle of placement for the acetabular cup (determined using the pre-determined computer model of the patient's anatomy and the pre-determined surgical plan), on the screen of the computer monitor. Although the 2D view in the computer monitor is not able to give the surgeon a clear idea of the proper positioning angle for the impactor in the 3D space of the real world, through some trial-and-error, the surgeon can eventually set the impactor at the desired angle of approach since the system does give substantially real-time feedback to the surgeon while the surgeon moves the actual impactor about the surgical site. Then the surgeon looks away from the computer monitor and back to the actual surgical scene, and hammers the proximal end of the impactor so as to insert the acetabular cup into place in the acetabulum. However, during this hammering, it is common for the angle of the impactor to change slightly and for the angle of the pelvis to change slightly. Unfortunately, the surgeon cannot check the angle of placement again until after the surgeon stops the hammering procedure and looks back up at the computer monitor. Thus, there is an opportunity for cup placement error to occur. Moreover, the surgeon can actually control the direction of the impaction with his/her impactor and mallet, but the computer monitor of the computer-guided system does not give the surgeon a clear idea of the ideal direction for the prosthetic cup during the hammering itself. Instead, the surgeon does not get this feedback until the surgeon looks back up at the computer monitor again and spends the time needed to interpret the 2D information presented on the computer monitor and correlate that information to the 3D setting of the real-world surgical scene. Thus, the opportunity for the surgeon to adjust the angle of impaction during hammering is generally lost.

Thus there is a need for a new way to guide the placement of an acetabular cup during a total hip arthroplasty procedure so as to improve the accuracy of the procedure.

SUMMARY OF THE INVENTION

The present invention provides a new way to guide the placement of an acetabular cup during a total hip arthroplasty procedure so as to improve the accuracy of the procedure.

More particularly, the present invention provides a visual guide to the surgeon, immediately adjacent to the surgical site, so as to assist the surgeon in accurately performing a surgical procedure, e.g., in accurately positioning the acetabular cup during a total hip arthroplasty procedure.

In one preferred form of the invention, there is provided a method for providing a visual guide to a surgeon, the method comprising:

identifying a desired axis for conducting a surgical procedure at a surgical site; and positioning an angle indicator adjacent to the surgical site, with the angle indicator being aligned with the desired axis.

In another preferred form of the invention, there is provided a computer-guided surgical system for identifying a desired axis for conducting a surgical procedure at a surgical site, the system comprising:

a robot having an active robot arm; and an angle indicator attached to the active robot arm;

wherein the robot is programmed to position the angle indicator adjacent to the surgical site, with the angle indicator being aligned with the desired axis.

In another preferred form of the invention, there is provided a method for providing a visual guide to a surgeon, the method comprising:

identifying a desired axis for conducting a surgical procedure at a surgical site; and positioning an angle indicator adjacent to the surgical site, with the angle indicator visually indicating the desired axis to the surgeon.

In another preferred form of the invention, there is provided a computer-guided surgical system for identifying a desired axis for conducting a surgical procedure at a surgical site, the system comprising:

a robot having an active robot arm; and an angle indicator attached to the active robot arm;

wherein the robot is programmed to position the angle indicator adjacent to the surgical site, with the angle indicator visually indicating the desired axis to the surgeon.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
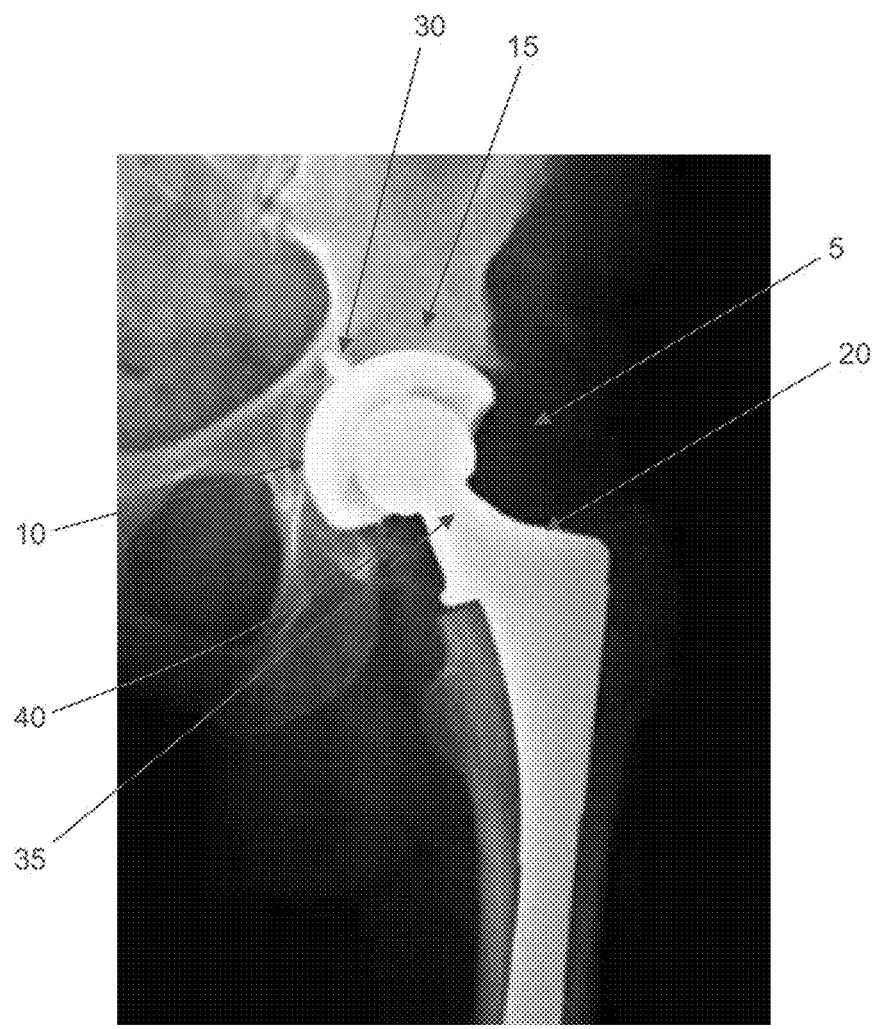
FIG. 1 is a schematic view showing a prosthetic total hip joint.
Figure 2:
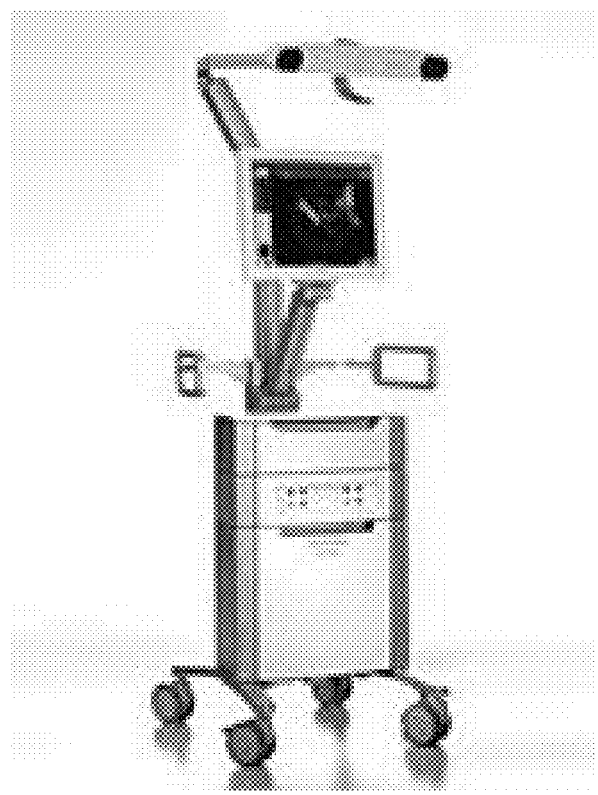
FIGS. 2-4 are schematic views showing prior art computer-guided surgical systems.
Figure 3:
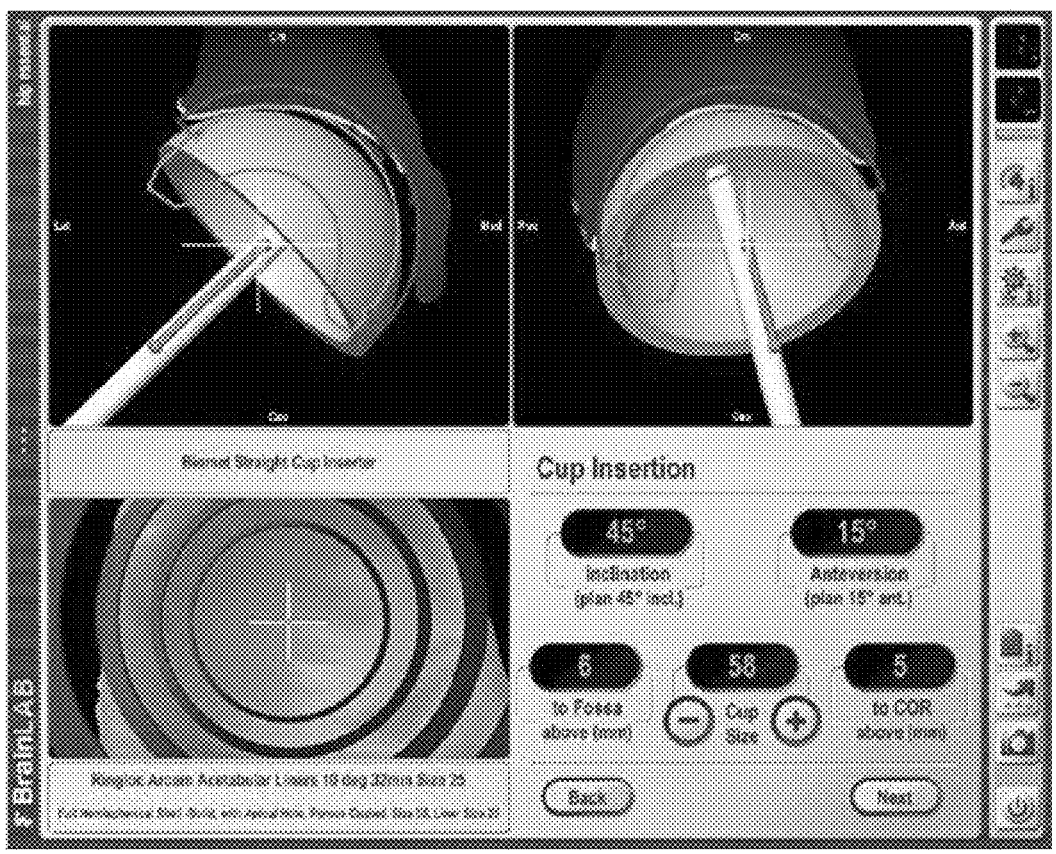
Figure 4:
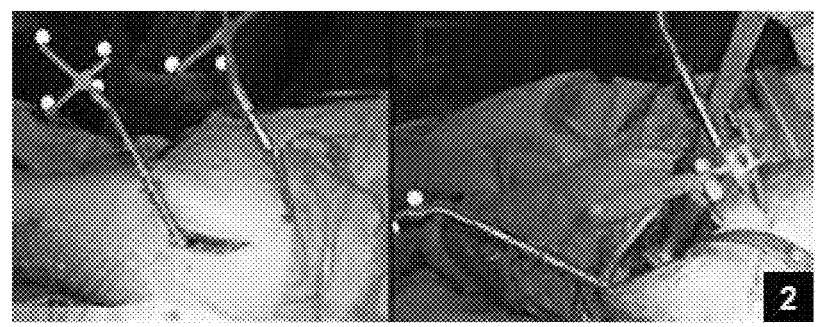

The present invention provides a new way to guide the placement of an acetabular cup during a total hip arthroplasty procedure so as to improve the accuracy of the procedure.

More particularly, the present invention provides a visual guide to the surgeon, immediately adjacent to the surgical site, so as to assist the surgeon in accurately performing a surgical procedure, e.g., in accurately positioning the acetabular cup during a total hip arthroplasty procedure.

In accordance with the present invention, the desired angle of the acetabular cup is indicated to the surgeon, directly at the real-world surgical scene, by appropriately positioning an angle indicator at the surgical scene. This angle indicator is automatically positioned at the surgical scene by the computer-guided surgical system, i.e., via an active robot arm. The surgeon then uses this angle indicator as a visual guide to correctly position the cup impactor prior to, and during, hammering of the prosthetic acetabular cup into position in the acetabulum. The results obtained by using this real-world guidance mechanism are maximized by locating the angle indicator immediately adjacent to the surgical site, so that the angle indicator becomes part of the surgical scene observed by the surgeon as the surgical procedure is performed.

In one preferred form of the invention, the angle indicator comprises an elongated rod. In this form of the invention, the computer-guided surgical system positions the elongated rod immediately adjacent to the surgical site, with the elongated rod being disposed parallel to, but laterally spaced from, the desired axis for cup placement. The surgeon then uses the elongated rod as a visual reference to guide proper placement of the cup impactor prior to, and during, cup hammering, i.e., by keeping the cup impactor parallel to the elongated rod.

This novel approach provides numerous benefits to the surgeon, including:
  cup alignment is intuitive and requires a minimal learning curve;
  surgical time with this new computer-guided surgical system is significantly shorter than with conventional computer-guided systems; and
  the surgeon can simultaneously look at both the surgical site and the angle indicator, thereby significantly improving alignment accuracy and reducing surgical error.

The present invention utilizes a robot to appropriately position the angle indicator adjacent to the surgical site, with the angle indicator being located on the end effector of the robot. The present invention preferably also includes a marker which can be fixed to the pelvis, and a 3D digitizing system to measure and track the pelvic marker and pelvic anatomical points (e.g., anatomical landmarks). All elements of the system are sterilizable.

The pelvic marker is preferably fixed to the pelvis via a known surgical method. Then the anatomical points of the pelvis (e.g., anatomical landmarks), and the location of the pelvic marker, are digitized. The anatomical points can be digitized by palpation. And when it is needed, the digitizing system tracks the location of the marker and, using this information, the robot brings the angle indicator (e.g., the aforementioned elongated rod) adjacent to the surgical site, aligning the angle indicator with the preferred angle for setting the acetabular cup. The surgeon then uses the angle indicator (e.g., the elongated rod) as a visual guide to aid the surgeon in the proper positioning of the impactor prior to, and during, hammering, whereby to guide proper positioning of the prosthetic acetabular cup in the acetabulum.

Significantly, the surgeon, the impactor and the acetabular cup do not need to actually contact the robot or the angle indicator (e.g., the elongated rod) at any time during the surgery—the surgeon simply aligns the long axis of the impactor with the long axis of the angle indicator (e.g., the elongated rod) prior to, and during, impaction. In one preferred form of the invention, the robot preferably places the angle indicator about 10 cm from the desired axis of the acetabular cup.

EXAMPLE

Figure 5:
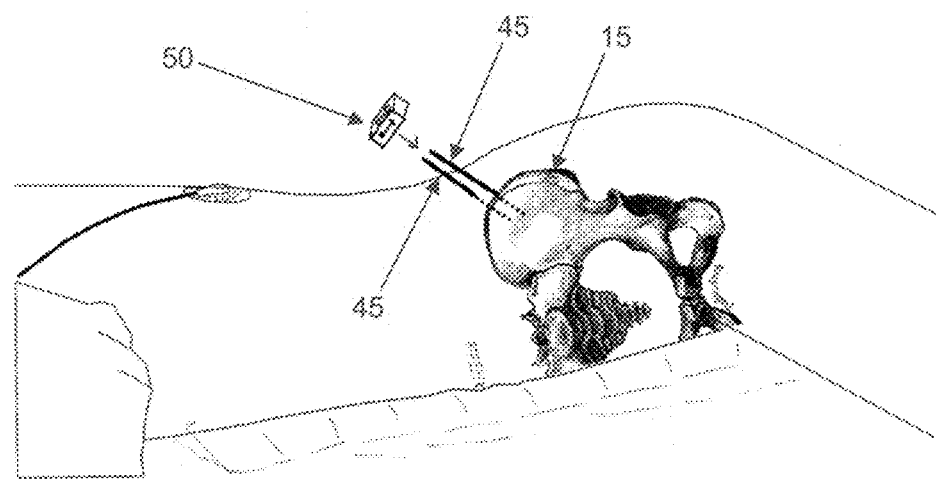
FIGS. 5-10 are schematic views showing one preferred form of the novel computer-guided surgical system of the present invention.

1. Installation Of The Pelvic Marker. After standard disinfection and preparation of the patient, the patient is laid in the lateral position, and two K-wires 45 (FIG. 5) are inserted into the pelvis 15 of the patient. Then a pelvic marker 50 is attached to the pelvis 15 using these two K-wires. This pelvic marker 50 provides a reference for the pelvis 15.

2. Digitization Of The Pelvic Marker And The Anatomical Landmarks, Setting The Pelvic Plane With Respect To The Pelvic Marker. The patient is laid in the supine position. Then the pelvic marker 50 is digitized, e.g., using a digitizer 55 (FIG. 6) mounted to a robot 58. See FIG. 6. This process recognizes the position and the direction of the pelvic marker 50 relative to the robot.

Then, without moving the patient, the surgeon digitizes an anatomical landmark 60 (FIG. 7) located on the pelvis 15 of the patient. Note that in FIG. 7, the anatomical landmark 60 is the left ASIS (i.e., the left anterior superior iliac spine).

Figure 8:
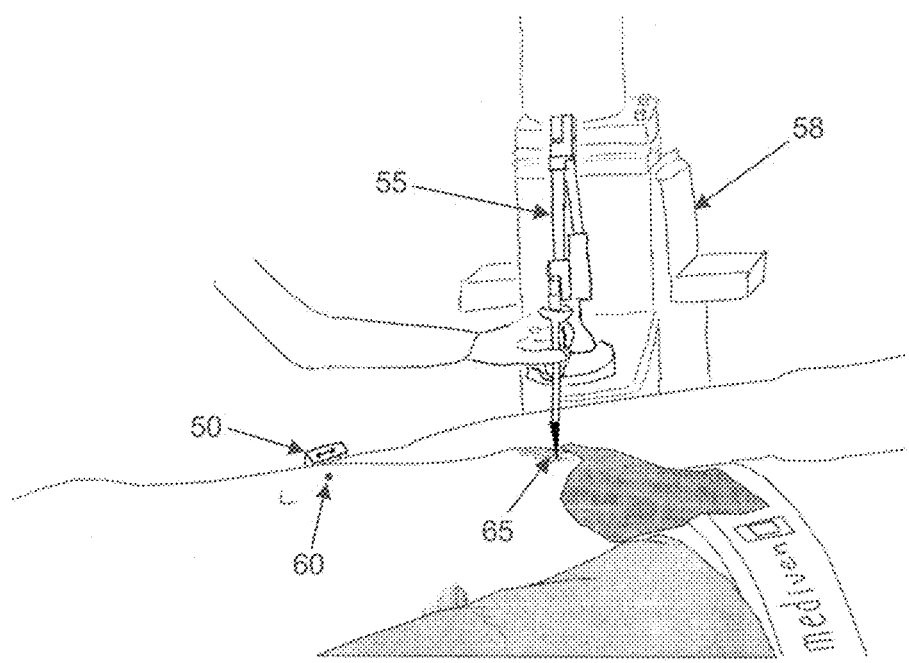

Next, and still without moving the patient, the surgeon digitizes another anatomical landmark 65 (FIG. 8). Note that in FIG. 8, the anatomical landmark 65 is the pubic point. Then, even though it is not illustrated here, the surgeon preferably digitizes another anatomical landmark, e.g., the right ASIS. Also, if necessary, the pelvic marker 50 can be digitized again so as to confirm that the patient has not moved significantly during the foregoing digitization process.

3. Reaming The Acetabulum. After the aforementioned digitization process, which allows the robot's pre-determined computer model of the patient's anatomy to be placed into proper registration with the real-world anatomy, the robot 58 is temporarily moved away from the surgical area. The surgeon then manually reams the acetabulum (e.g., with a manual reamer) so as to prepare the seat in the acetabulum for the prosthetic acetabular cup.

Figure 9:
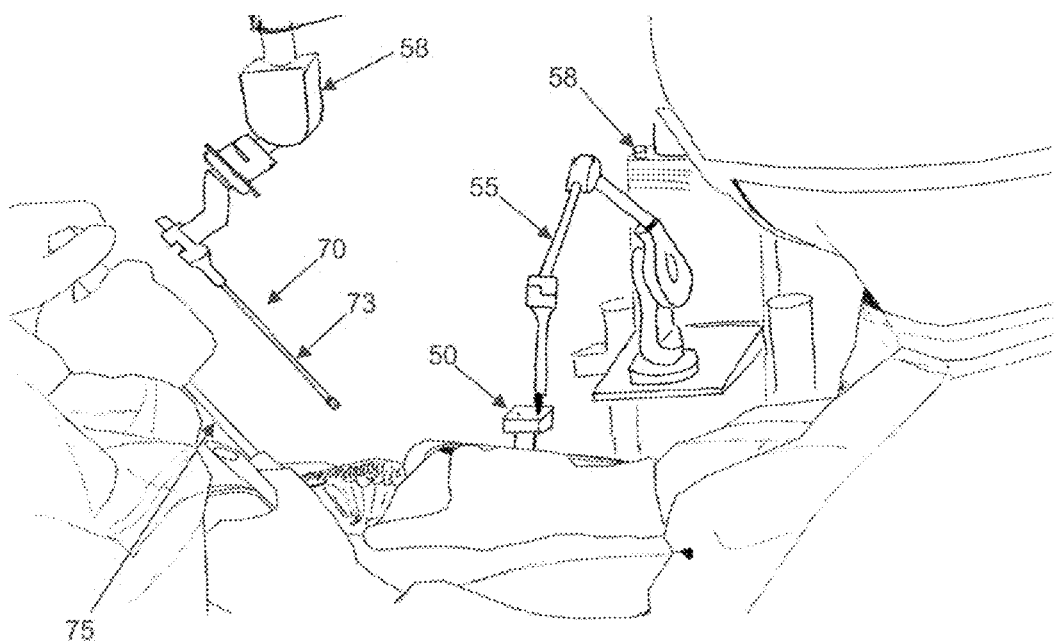
Figure 10:
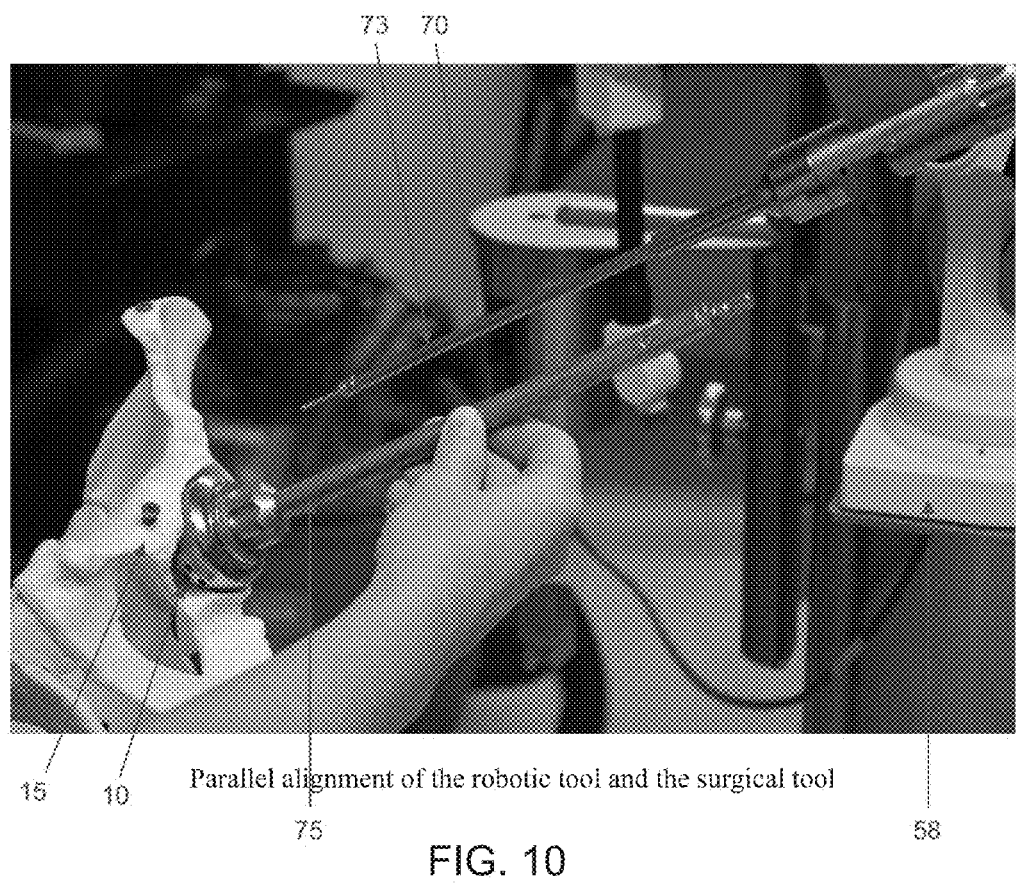

4. Setting The Acetabular Cup. After the acetabulum has been prepared, the robot 58 is moved back to the surgical area. When the acetabular cup is to be set in the acetabulum, the position of the pelvic marker 50 is digitized again (unless a digitizer has been connected to the pelvic marker 50 for continuous measurement of anatomy position). Then, based on the pelvic plane and the pre-planned angle for the acetabular cup, the robot 58 positions an angle indicator 70 (FIG. 9), which is located at the effector end of the robot 58, adjacent to the surgical site, so that the angle indicator can act as a visual guide to show the proper insertion angle to the surgeon. In one preferred form of the invention, the angle indicator 70 comprises an elongated rod 73. In this form of the invention, the robot 58 positions the elongated rod 73 immediately adjacent to the surgical site, with the elongated rod 73 being disposed parallel to, but laterally spaced from, the desired axis for cup placement. The surgeon then aligns the impactor 75 with the robot's angle indicator 70 (e.g., the elongated rod 73) and hammers the free end of the impactor 75 so as to set the acetabular cup in the pelvis. See FIG. 10. As this occurs, the robot's angle indicator 70 (e.g., the elongated rod 73) does not physically contact the patient, and the robot's angle indicator 70 (e.g., the elongated rod 73) does not physically contact the impactor.

Additional Aspects of the Invention

Thus it will be seen that, with the present invention, the robot does not mill the acetabular cavity, nor does the robot insert the acetabular cup into the acetabulum. Rather, the robot simply positions the angle indicator 70 (e.g., the elongated rod 73) adjacent to the surgical site so as to visually guide the surgeon in the proper disposition of the prosthetic acetabular cup. It is the surgeon's responsibility to visually observe the disposition of the robot's angle indicator 70 (e.g., the elongated rod 73) and manually position the impactor 75 at a parallel angle to the robot's angle indicator 70 (e.g., the elongated rod 73), whereby to properly seat the acetabular cup in the acetabulum.

Significantly, the aforementioned acetabular cup guidance function of the present invention can be easily incorporated into the Robodoc® surgical robot currently available from Curexo Technology Corp. of Fremont, Calif. In this configuration, the Robodoc® robot can first be used in its conventional manner to prepare (i.e., cut) the femoral side of the total hip arthroplasty, and then also used in the novel manner disclosed above for guiding proper placement of the acetabular cup in the pelvis.

Alternatively, the Robodoc® robot can be used only for the guidance function of the present invention, i.e., to properly position the angle indicator 70 (e.g., the elongated rod 73) so as to guide the surgeon in the proper placement of the prosthetic acetabular cup in the acetabulum.

It will be appreciated that the present invention provides a much more intuitive approach for aligning the cup impactor 70 than conventional computer-guided surgical systems—in a conventional computer-guided surgical system, the surgeon must continually check the computer monitor, which only provides a 2D image, in order to set the real-world (3D) orientation for the impactor, and hence set the real-world (3D) orientation for the acetabular cup. Thus, the present invention provides a much simpler and more readily understandable visual guide for the surgeon. Furthermore, the present invention provides this visual guide right at the surgical site and is located so that it is incorporated directly into the surgical scene, and is not located on a remote computer monitor.

Furthermore, by using a CT image of the anatomy, it is possible to measure the soft tissue thickness at the ASIS and pubic points, and this soft tissue thickness can be accounted for when forming a surgical plan.

And where the present invention is incorporated into the Robodoc® surgical robot currently available from Curexo Technology Corp., anteversion of the femoral stem is precisely controlled by Robodoc® preparation, thus ensuring that the arthroplasty remains in the "safe zone" and patient-specific anatomy can be accounted for.

Of course, it will be appreciated that the present invention does not guarantee perfect accuracy in setting the acetabular cup into the pelvis. Significant error may still occur if the aforementioned digitization process is not accurate, or if the patient moves significantly after digitization, or if the surgeon does not properly follow the visual guide provided by the present invention at the surgical site. However, the present invention is significantly easier and safer to use, and more accurate, than the conventional computer-guided surgical systems currently available. Moreover, the present invention is significantly more accurate than setting the acetabular cup "by eye", i.e., without the use of a computer-guided surgical system.

Further Aspects of the Invention

The Robodoc® surgical robot currently available from Curexo Technology Corp. is a robotic surgical system for cutting and shaping bone for the femoral preparation in a total hip arthroplasty procedure. The Robodoc® surgical robot provides for very accurate femoral shaping.

The present invention provides for accurate placement of the acetabular cup and has been described above. The present invention may be embodied in a self-standing robotic system.

It is anticipated that there may be surgeons who wish to use the Robodoc® surgical robot for femoral preparation, and use a self-standing implementation of the present invention for guided seating of the acetabular cup. However, because of the cost of providing two separate systems, and because of space limitations in the operating room, the use of two such self-standing systems in a single surgery is generally not desirable. Thus, it would be desirable to add the aforementioned acetabular cup guidance function of the present invention to the current Robodoc® surgical robot.

Figure 6:
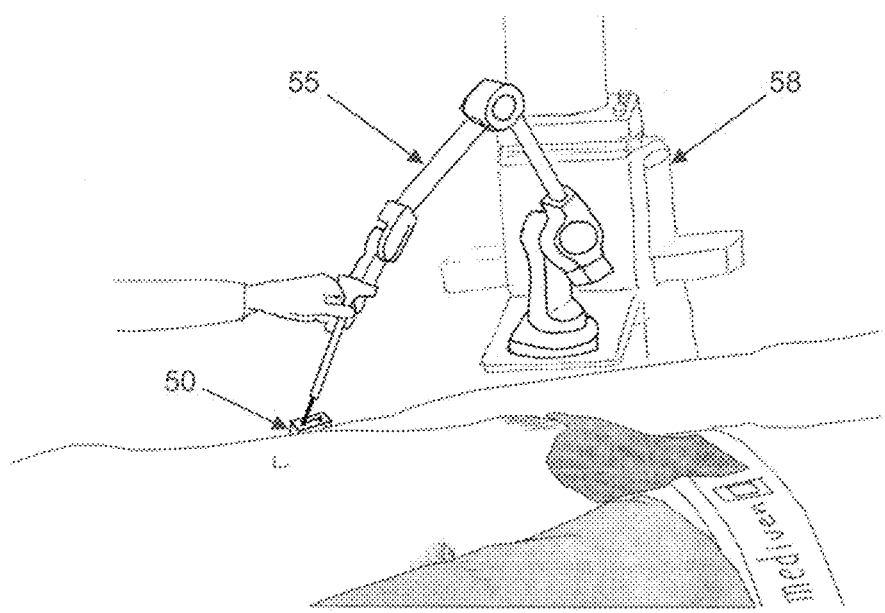
Figure 7:
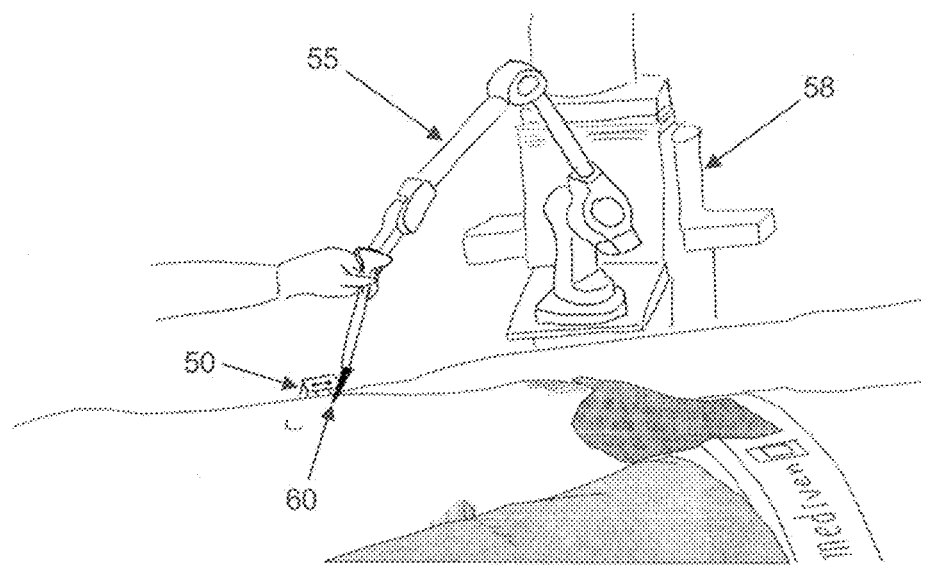

To this end, the current Robodoc® surgical robot uses an articulated digitizing arm for digitization of real-world structures. Thus, in the foregoing example, an articulated digitizing arm 55 has been used to digitize and track the anatomy of the patient (FIGS. 6-8). But in broader aspects of the invention, any system which is able to measure and track the real-world position of structures may be utilized in place of the articulated digitizing arm 55. By way of example but not limitation, the present invention may utilize magnetic field detection trackers such as the Polhemus system, high-resolution optical camera systems, etc.

Figure 11:
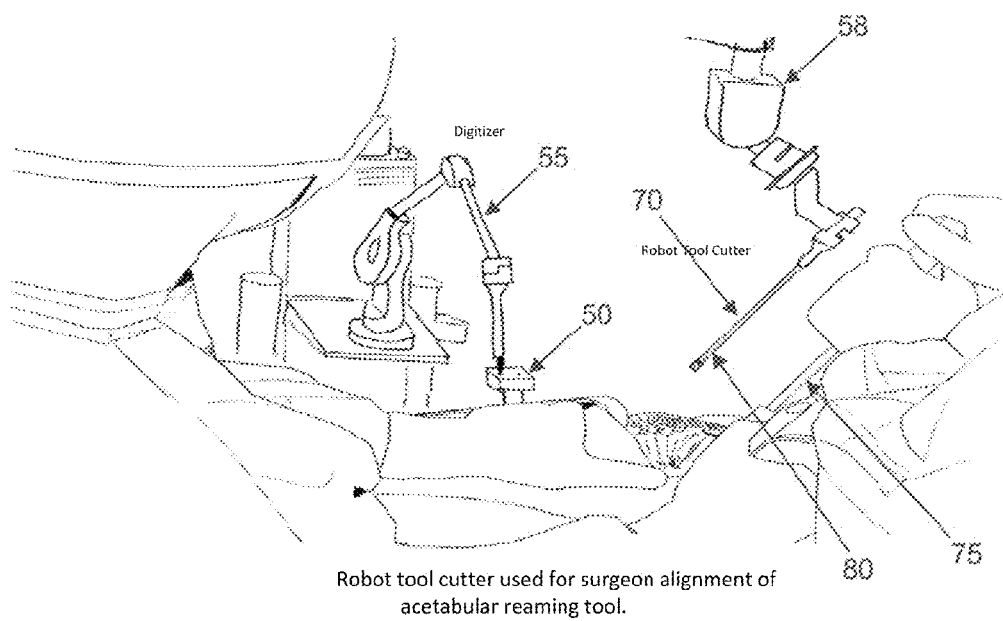
FIG. 11 is a schematic view showing another preferred form of the novel computer-guided surgical system of the present invention.

Also, the Robodoc® surgical robot is equipped with a long surgical cutter 80 (FIG. 11), approximately 10 inches long, to shape the bone. Because this surgical cutter 80 has an elongated linear shape, highly similar to the elongated rod 73 discussed above, the surgical cutter 80 can easily be used as the angle indicator 70 for the aforementioned acetabular cup guidance function. But in this respect it should also be appreciated that the angle indicator 70 does not necessarily have to be an elongated rod. For example, some surgical tools are bent because of limitations in the surgical approach. In such a circumstance, the angle indicator 70 can also be bent so as to give a better visual indication to the surgeon. Furthermore, the angle indicator 70 can be a substantial replica of a surgical tool, e.g., the angle indicator 70 can be a substantial replica of the impactor 75 which is used to set the acetabular cup.

For the measurement and digitization of the pelvis and the pelvis reference plane, and the determination of the preferred angle for setting the acetabular cup, the foregoing description was kept relatively brief in order not to detract from the novel aspects of the present invention. However, it will be appreciated that various approaches are well known in the art for such measurement, digitization and angle calculation (e.g., using a pre-operatively installed pin with CT scan, a CT scan with bone digitization and kinematic registration, etc.), and the present invention is intended to encompass any and all such approaches for measurement, digitization and angle calculation.

Also, in the foregoing description of the present invention, there was no mechanical interaction between the impactor 75 and the angle indicator 70 (e.g., the elongated rod 73). However, if desired, such mechanical interaction can be implemented with the present invention.

Additionally, in the foregoing description of the present invention, the method used to calculate the acetabular cup angle from the pelvic marker and anatomic points was not presented, since it can be easily calculated by an engineer skilled in the art. But it is notable that in the current embodiment of the present invention, the robot is intended to show direction only, so that the position of the robot is not restricted. For example, the robot can be back-drivable, or the robot can use a force-feedback system, so that the surgeon can move the robot to a convenient location (e.g., out of the way of the surgeon) while the angle of the visual indicator 70 is kept constant by the robot.

In addition to the foregoing, the ideal or preferred angle for the acetabular cup is dependent on the patient anatomy and on the positioning of the femoral implant and, in this respect, it should be appreciated that the positioning of the acetabular cup can be more closely controlled using the present invention. More particularly, conventional acetabular cup guidance systems are not able to control placement of the femoral implant, and inasmuch as the conventional acetabular cup guidance systems do not require CT data, the preferred cup angle is not based on the patient anatomy. But the Curexo Robodoc® surgical robot already requires a CT scan of the patient, and placement of the femoral implant is precisely controlled by the Robodoc® surgical robot. As a result, when the present invention is implemented in conjunction with the Robodoc® surgical robot, the surgeon can actually "customize" the ideal angle of the acetabular cup based on the patient anatomy, and based on the placement of the femoral implant, in the pre-operative procedure. Also, the surgeon can even "simulate" the prosthetic joint's range of motion, and check his/her surgical plan, before surgery is commenced. Thus, where the present invention is combined with a system (such as the Robodoc® surgical robot) which already provides a CT scan of the patient's anatomy and a bone-cutting surgical robot, it is possible to pre-operatively customize planning of the acetabular angle.

Furthermore, for easier alignment of the impactor 75 with the angle indicator 70 (e.g., the elongated rod 73), a flexible guide can be provided. More particularly, it is believed that trained orthopedic surgeons will generally be comfortable aligning a surgical tool with an adjacent guide (e.g., the elongated rod 73) via the visual inspection approach discussed above. Thus it is believed that it will be sufficient for the surgeon to align the impactor 75 with the angle indicator 70 (e.g., the elongated rod 73) via a simple visual inspection. However, it is also believed that a flexible mechanical guide can be provided to further assist in aligning the impactor 75 with the angle indicator 70.

Figure 12:
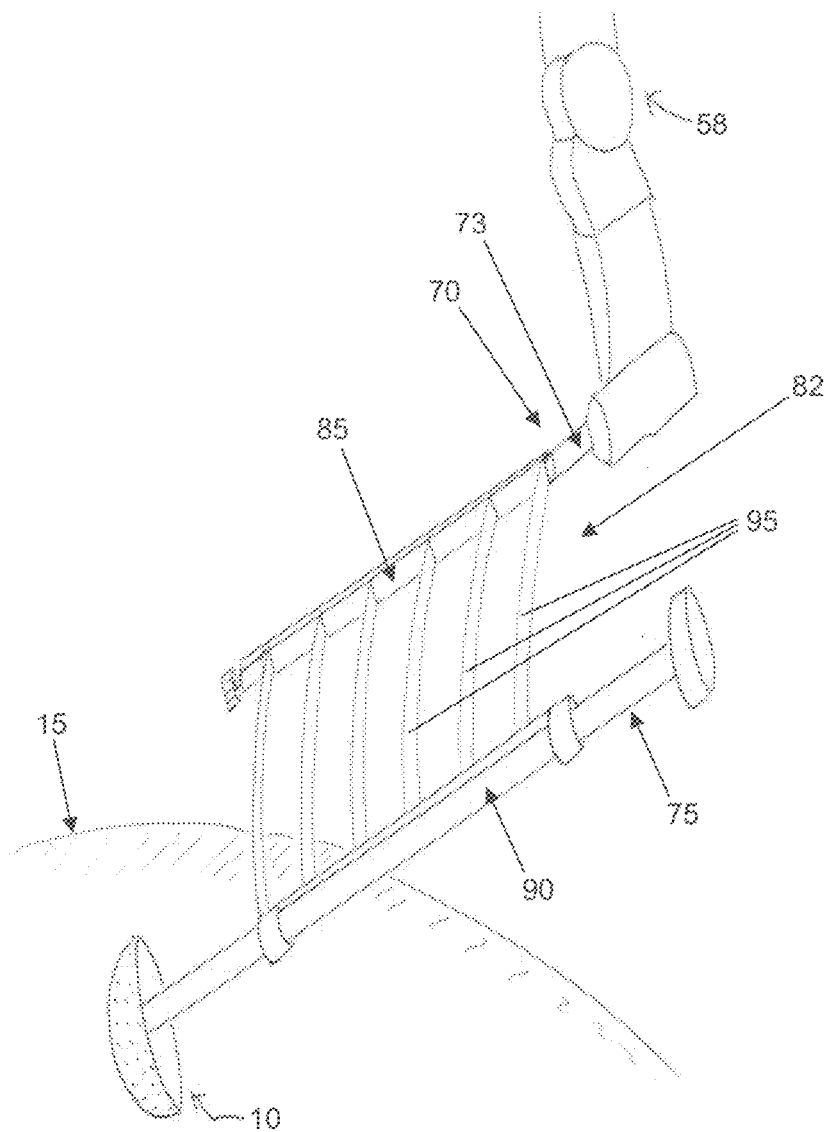
FIG. 12 is a schematic view showing still another preferred form of the novel computer-guided system of the present invention.

To that end, and looking now at FIG. 12, there is shown an exemplary guide 82 which may be used for this purpose. The guide 82 is preferably disposable and made from thin plastic. It should be appreciated that the guide 82 shown in FIG. 12 primarily gives visual guidance to the surgeon as to when impactor 75 and the angle indicator 70 (e.g., the elongated rod 73) are not in parallel disposition, rather than giving significant mechanical guidance to the disposition of the impactor 75. More particularly, in the guide 82 shown in FIG. 12, the guide is made of a thin plastic tape which is quite flexible. The tape is composed of three parts: the adhesive part 85 which connects to the robotic angle indicator 70 (e.g., the elongated rod 73), the band part 90 which connects to the surgical impactor 75, and wings 95 which extend between the two parts. Thus, the tape is attached to both the impactor 75 and the robotic angle indicator 70 (e.g., the elongated rod 73). If the manual impactor 75 and the robotic angle indicator 70 are disposed in parallel disposition, the wings 95 will also be in parallel dispositions; but if the manual impactor 75 and the robotic angle indicator 70 are not in parallel disposition, the wings 95 will be distorted and the space between the wings will not be identical, which provides the surgeon with a good visual indication of the alignment (or mis-alignment) of the manual impactor 75 vis-à-vis the robotic angle indicator 70.

Additionally, in the foregoing description, the angle indicator 70 is sometimes discussed in the context of an elongated rod 73, i.e., a physical object having an elongated structure somewhat analogous to the shaft of the impactor. However, it is also possible for the angle indicator to be provided at the surgical site by other means.

Figure 13:
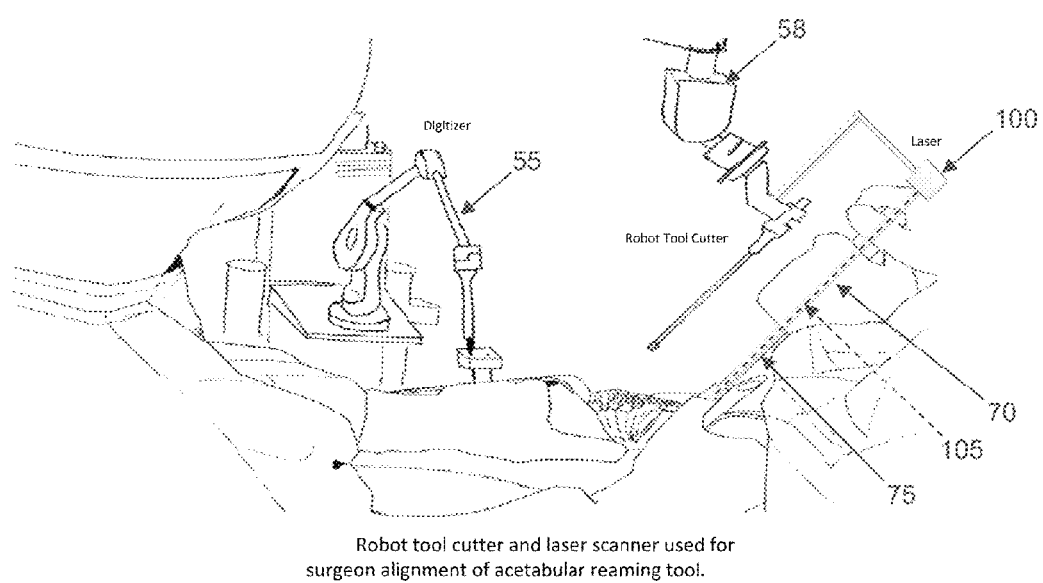
FIG. 13 is a schematic view showing yet another preferred form of the novel computer-guided surgical system of the present invention.

By way of example but not limitation, in FIG. 13, angle indicator 70 comprises a laser 100 providing a visible laser beam 105. In this form of the invention, the surgeon aligns impactor 75 parallel to the laser beam 105, in a manner analogous to how the surgeon aligns impactor 75 parallel to elongated rod 73.

Figure 14:
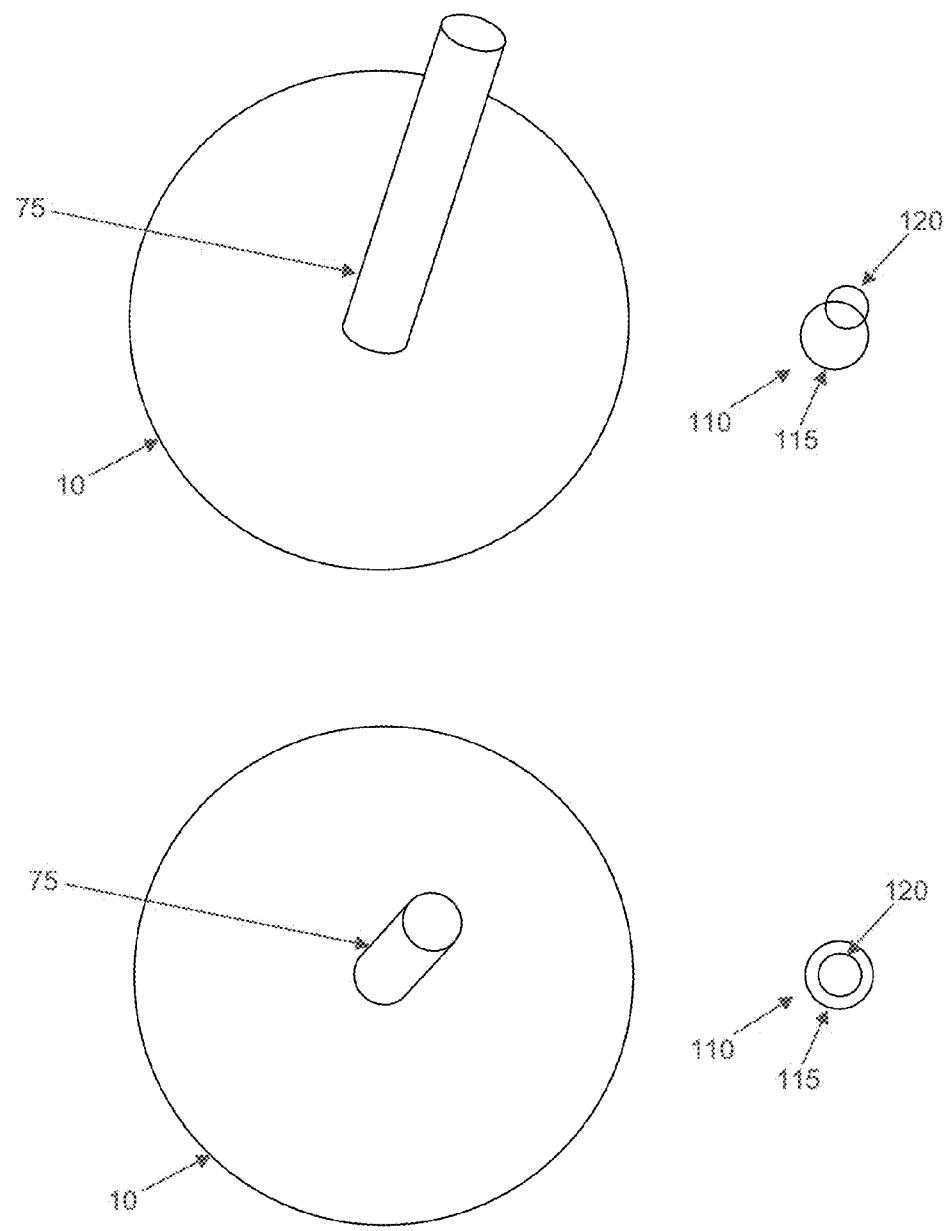
FIG. 14 is a schematic view showing another preferred form of the novel computer-guided surgical system of the present invention.

By way of further example but not limitation, in FIG. 14, angle indicator 70 comprises a laser sight 110 which is projected onto the surgical site, adjacent to the prosthetic acetabular cup 10 and impactor 75. In this form of the invention, the laser sight 110 comprises a pair of circles 115, 120: when the impactor 75 is properly aligned with the desired angle of cup placement, the laser circles 115, 120 are concentric with one another; but when the impactor 75 is not properly aligned with the desired angle of cup placement, laser circles 115, 120 are not concentric with one another.

Still other forms of visual indicators will be apparent to those skilled in the ark in view of the present disclosure.

Use of the Present Invention for Other Applications

It should be appreciated that, in addition to setting the acetabular cup in a total hip arthroplasty procedure, the present invention may also be used for guiding other procedures within the hip joint. Additionally, the present invention may be used for guiding procedures within joints other than the hip joint (e.g., it may be used to guide procedures in the knee joint, the shoulder joint, etc.). Furthermore, the present invention may be used to guide procedures in areas other than a joint, and/or to guide procedures on tissue other than bone, e.g., the present invention may be used to guide a surgical procedure on soft tissue within the chest cavity.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the present invention.

What is claimed is:
1. A method for providing a visual guide to a surgeon performing a surgical procedure at a surgical site using a surgical instrument, the method comprising:

identifying a desired axis for conducting the surgical procedure at the surgical site using the surgical instrument; and positioning an angle indicator adjacent to the surgical site, using a robot operating according to a pre-determined surgical plan, so that the angle indicator is aligned with the desired axis, with the angle indicator being independent of the patient anatomy, and with the angle indicator being independent of the surgical instrument, whereby the surgeon may thereafter perform the surgical procedure with the surgical instrument along the desired axis by manually aligning the surgical instrument with the adjacent angle indicator while performing the surgical procedure.

2. A method according to claim 1 wherein the surgical procedure comprises deployment of a prosthetic acetabular cup in the acetabulum of the hip.

3. A method according to claim 1 wherein the angle indicator comprises a physical object.

4. A method according to claim 3 wherein the physical object has a visual similarity to an impactor used to set the prosthetic acetabular cup in the acetabulum of the hip.

5. A method for performing a surgical procedure at a surgical site using a surgical instrument, the method comprising:

identifying a desired axis for performing the surgical procedure at the a surgical site using the surgical instrument;

positioning an angle indicator adjacent to the surgical site, using a robot operating according to a pre-determined surgical plan, so that, the angle indicator is aligned with the desired axis, with the angle indicator being independent of the patient anatomy, and with the angle indicator being independent of the surgical instrument; and performing the surgical procedure with the surgical instrument along the desired axis by manually aligning the surgical instrument with the adjacent angle indicator while performing the surgical procedure.

6. A method according to claim 5 wherein the surgical procedure comprises deployment of a prosthetic acetabular cup in the acetabulum of the hip.

7. A method according to claim 5 wherein the angle indicator comprises a physical object.

8. A method according to claim 7 wherein the physical object has a visual similarity to an impactor used to set the prosthetic acetabular cup in the acetabulum of the hip.

* * * * *